United States Patent [19]
Cattelin

[11] Patent Number: 6,143,792
[45] Date of Patent: Nov. 7, 2000

[54] USE OF A SPECIFIC ANTAGONIST OF 5HT$_2$ RECEPTORS FOR PREPARAING MEDICINES USEFUL FOR TREATING SLEEP-DISORDERED BREATHING

[75] Inventor: Françoise Cattelin, Paris, France

[73] Assignee: Sanofi-Synthelabo, Paris, France

[21] Appl. No.: 09/446,484

[22] PCT Filed: Jun. 2, 1998

[86] PCT No.: PCT/FR98/01100

§ 371 Date: Mar. 27, 2000

§ 102(e) Date: Mar. 27, 2000

[87] PCT Pub. No.: WO99/00119

PCT Pub. Date: Jan. 7, 1999

[30] Foreign Application Priority Data

Jun. 26, 1997 [FR] France ................... 97 07998

[51] Int. Cl.⁷ .................. A61K 31/15; C07C 251/58
[52] U.S. Cl. ............................ 514/640; 564/256
[58] Field of Search ................ 564/256; 514/640

[56] References Cited

U.S. PATENT DOCUMENTS 5,166,416  11/1992  Congy et al. ............... 549/59
5,290,951   3/1994  Congy et al. ............... 549/59

FOREIGN PATENT DOCUMENTS 0 373 998   6/1990   European Pat. Off. .
0 449 561  10/1991   European Pat. Off. .
0 518 767  12/1992   European Pat. Off. .

OTHER PUBLICATIONS

M. Yoshioka et al., J. Pharmacol. and Exp. Therapeutics, vol. 260, No. 2 pp. 917–924 (1992).
S. Veasey et al. Am. J. of Resp. and Critical Care Med., vol. 153, No. 2, pp. 776–786 (1996).
M. Rinaldi–Carmona et al., Life Sciences, vol. 54, pp. 119–127 (1993).
G. Loas, L'Encéphale, XVII, pp. 423–425 (1991).
R. Monteau, European Journal of Pharmacology, vol. 259, pp. 71–74 (1994).
H. S. Schmidt, Bulletin European Physiopath. Resp., vol. 19, pp. 625–629, (1983).
D. Hanzel, et al., Chest, vol. 100, No. 2, pp. 416–421 (1991).
M. Rinaldi–Carmona et al., J. Pharmacol. and Exp. Thera., vol. 262, No. 2, pp. 759–768 (1992).
D. Rose et al., Fundamental and Clinical Pharmacology, vol. 10, No. 1, p. 80 (1996).
T. Young et al., The New England Journal of Med., vol. 328, No. 17, pp. 1230–1235 (1993).
D. Hudgel, Chest, vol. 109, No. 5, pp. 1346–1358, (1996).

*Primary Examiner*—Peter O'Sullivan
*Attorney, Agent, or Firm*—Michael D. Alexander; Paul E. Dupont

[57] ABSTRACT

The invention relates to the use of a specific 5HT2 receptor antagonist for the preparation of medicines useful in the treatment of the sleep apnea syndrome.

4 Claims, No Drawings

USE OF A SPECIFIC ANTAGONIST OF 5HT$_2$ RECEPTORS FOR PREPARAING MEDICINES USEFUL FOR TREATING SLEEP-DISORDERED BREATHING

This application is a 371 of PCT/FR 98/01100 filed Jun. 2, 1998.

The present invention relates to a novel use of a specific 5HT$_{2A}$ receptor antagonist.

1-(2-fluorophenyl)-3-(4-hydroxyphenyl)-prop-2-en-1-one-O-2-dimethylamino ethyl)-oxime of formula (I) and its pharmaceutically acceptable salts are described in the European patent 0 373 998 B1 as 5HT$_2$ receptor to antagonists:

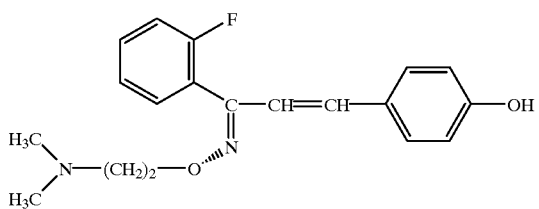

(I)

More particularly, the hemifumarate of (1Z, 2E)-1-(2-fluorophenyl)-3-(4-hydroxyphenyl)-prop-2-en-1-one-O-(2-dimethylaminoethyl)-oxime, known under the code name SR 46349 B and hereafter designated compound A, has been studied with respect to its pharmacological and biochemical properties. Compound A is a specific 5HT$_{2A}$ receptor antagonist, in that it has no affinity for the 5HT$_{1A}$, 5HT$_{1B}$ and 5HT$_{1D}$ receptors and a slight affinity for the 5HT$_{2C}$ receptor; in studies on isolated tissues, the absence of activity of compound A on the stomachal fundus of the rat indicates a 5HT$_{2A}$ versus 5HT$_{2B}$ specificity (M. Rinaldi-Carmona et al., J. Pharmacol. Exp; Ther., 1992, 262, 2, 759–768). In the rodent, it has been shown that this compound binds mainly to the brain regions containing the 5HT$_2$ receptor (M. Rinaldi-Carmona et al., Life Sciences, 1993, 54, 119–127).

Studies on sleep have shown that certain 5HT$_2$ receptor antagonists like ritanserin, amoxapine and ICI 169 369 modify the architecture of sleep and regulate or increase the time of slow-wave sleep (G. Loas, L'encéphale, 1991, XVII, 423–425)

The central mechanisms by which serotonin modulates respiratory activity have been studied and it was found that, among the different families of receptors, only the 5HT$_1$ receptors and the 5HT$_2$ receptors have a central effect on respiratory activity (R. Monteau et al., Eur. J. Pharmacol., 1994, 259, 71–74).

In the same article, these authors studied, in vitro, on tissue preparations from newborn rats, with the aid of compound A, which receptor subtypes are implicated in the modulation of respiratory activity. They observed that pretreatment with compound A prevents or significantly reduces the cervical tonic activity induced by 5-hydroxytryptamine and attributed to the activation of the 5HT$_2$ spinal receptors; similarly, it inhibits the depressor effect of 5-hydroxytryptamine on the activity of the hypoglossal nerve. Moreover, the authors suggest that compound A might be used for the in vivo study of the mechanisms responsible for obstructive apnea.

The use of L-tryptophan, a precursor of serotonin, in the respiratory disorders of sleep has been studied (H. S. Schmidt, Bull. Eur. Physiopathol. Respir., 1983, 19, 625–629) as well as that of fluoxetine, a selective inhibitor of serotonin recapture (Hanzel D. A., Chest, 1991, 100, 416–421).

The European patent application EP 449 561 A indicates the use of (R)-fluoxetine for the treatment of different diseased states, including sleep apneas.

An article by M. Yoshioka et al. in J. Pharmacol. Exp. Ther., 1992, 260 (2), 917–924 relates to the pharmacological characterization of the apnea induced by 5-HT in the rat; it reports that 5HT$_2$ receptor antagonists such as ketanserin and methysergide inhibit apnea induced by 5-HT, suggesting that the apnea induced by 5-HT is mediated by the inhibition of the afferent phrenic nerve activity.

In a recent article, S. C. Veasey et al. (Am; J. Respirat. Critic. Care Med., 1996, 153, 776–786) studied the effects of two serotonin antagonists in an animal model of respiratory disorders of sleep : the English bulldog. They conclude that ritanserin and methysergide, which antagonize 5HT$_2$ receptors in particular, when administered systemically, lead to a marked diminution of the dilating muscle activity of the upper airways and to a slight diminution of the activity of the diaphragm, these diminutions coinciding with oxyhemoglobin desaturations. The authors suggest that serotonin might play a role in increasing the dilating activity of the upper airways which is known to be implicated in the sleep apnea syndrome.

D. Rose et al. (Fundam. Clin. Pharmacol.,1996, 10 (1), 80) report the results of in vivo studies performed on decerebrated newborn animals (rats and cats). In the cat, they observed that the administration of high doses of 5-hydroxytryptamine induces prolonged central apneas linked to periods of active expiration. In the rat they did not observe apnea after administration of 5-hydroxytryptamine, which is in contradiction with the results observed in vitro in the newborn rat.

The interspecies differences observed on the respiratory mechanisms as well as the differences between the results of the in vivo and in vitro studies in the rat do not give any indication to the person skilled in the art of the possible effect of compound (I) on sleep apnea.

Unexpectedly, it has now been found that the compound of formula (I), in particular compound A, a 5HT$_{2A}$ receptor serotonin antagonist is efficacious in the treatment of the sleep apnea syndrome.

Thus, the present invention relates to the use of a compound of formula (I) for the preparation of medicines useful in the treatment of the sleep apnea syndrome, in particular the sleep obstructive apnea-hypopnea syndrome.

The sleep apnea syndrome is defined by cessation (apnea) or a diminution (hypopnea) of breathing recurring during sleep. The hypopneas and apneas occur during both paradoxal sleep and slow-wave sleep. Repeated cessation of breathing induces a diminution in the oxyhemoglobin saturation (SaO2) and wakenings lead to a fragmentation of sleep and to the disappearance of stages 3 and 4 corresponding to deep slow-wave sleep. The clinical consequences of this syndrome include:

i) an increase in the susceptibility to cardiovascular complications such as pulmonary hypertension, cardiac insufficiency, hypertension, cardiac arrhythmias, cerebral vascular accidents and myocardial infarction;

ii) excessive somnolence during the day and, secondarily, risks of accidents.

Furthermore, the fragmentation of sleep and the nocturnal desaturation of oxyhemoglobin cause fatigue, irritability, morning headaches, memory disorders and/or personality disorders.

Recent epidemiological data indicate that this syndrome seems to affect 2% to 4% or more of the adult population; men and obese people being particularly affected (New Engl. J. Med., 1993, 328 (17), 1230–1235).

At present the principal treatment prescribed, apart from loss of weight and surgery, is mechanical treatment by ventilation by continuous positive pressure (cpp). The principle of this last treatment (cpp) is based on the administration by the nasal route of positive expiratory and inspiratory pressure with the aim of suppressing the collapse of the upper airways. This treatment is cumbersome, noisy and restrictive, obliging the patient to wear a nasal mask every night; in addition, it has side effects such dry mouth, sneezing, nose bleeding or aerophagia. At present, there is no known treatment by a pharmacological agent (D.W. Hudgel, Chest, 1996, 109/5, 1346–1358).

It has now been found that the compound of formula (I), in particular compound A, is active in man in the treatment of the sleep apnea syndrome.

In young healthy subjects (18 to 35 years), it has been observed that the administration of compound A induces a doubling of the duration of stages 3 and 4 of slow-wave sleep at a dose of 1 mg; stages 1 and 2 of slow-wave sleep is slightly diminished and paradoxal sleep is unchanged.

The effect of compound A on patients suffering from sleep apnea is determined during a clinical study conducted in double blind versus placebo.

The patients participating in this study have an apnea-hypopnea index greater than 25 and also exhibit symptoms such as diurnal somnolence, hypertension, fatigue, morning headache, nycturia etc.

Apnea is defined as the absence of nasobuccal aerial flux for at least 10 seconds. Hypopnea is defined as a reduction by at least 50% of the nasobuccal aerial flux for at least 10 seconds. The apnea-hypopnea index (AHI) is the number of apneas and hypopneas occurring per hour. This index is obtained by a polysomnographic recording which also measures the ventilated output, the esophageal pressure and the oxyhemoglobin saturation ($SaO_2$).

A capsule containing 5 mg of compound A is administered with the evening meal every day for 14 days. A marked diminution of the apnea-hypopnea index in the subjects treated is observed.

Thus, the object of the present invention is the use of a compound of formula (I) for the preparation of medicines useful in the treatment of the sleep apnea syndrome.

The compound of formula (I) and its pharmaceutically acceptable salts are prepared according to the description given in the European patent 0 373 998 B1.

In the pharmaceutical compositions of the present invention for oral, sublingual, subcutaneous, intramuscular, intravenous, transdermal, topical or rectal administration, the active ingredient alone or in combination with another active ingredient may be administered in a unit form of administration, in an ad mixture with standard pharmaceutical vehicles, to animals and humans. Appropriate unit forms of administration include forms for the oral route such as tablets, capsules, powders, granules and oral solutions or suspensions; sublingual and buccal forms of administration; aerosols; implants; subcutaneous; intramuscular; intravenous; intranasal forms of administration and rectal forms of administration.

In the pharmaceutical compositions of the present invention the active ingredient is usually formulated in dose units. The dose unit contains from 0.05 to 50 mg, advantageously from 0.1 to 10 mg, preferably from 0.5 to 5 mg of $5HT_{2A}$ receptor antagonist per dose unit for daily administrations.

When a solid composition is prepared in the form of a tablet, it is possible to add to the active ingredient, micronized or not, a wetting agent and the whole is mixed with a pharmaceutical vehicle such as silica, starch, lactose, magnesium stearate, talc or the like. It is possible to coat the tablets with sugar, various polymers or other suitable materials or even treat them so that they have a prolonged or delayed action and so that they release a predefined quantity of active ingredient continuously.

A preparation of capsules is obtained by mixing the active ingredient or the active ingredients with a diluent and by incorporating the mixture obtained in soft or hard capsules.

A preparation in the form of a syrup or elixir may contain the active ingredient or active ingredients together with a sweetening agent, preferably calorie-free, methylparaben or propylparaben as antiseptics, as well as a flavouring agent or a suitable colouring matter.

The powders or granules dispersible in water may contain the active ingredient in a mixture with dispersion agents or wetting agents or suspending agents like polyvinylpyrrolidone or polyvidone, as well as with sweetening agents or flavour correctors.

For rectal administration, use is made of suppositories which are prepared with binders melting at the rectal temperature, for example cocoa butter or polyethyleneglycols.

For parenteral administration, use is made of aqueous suspensions, isotonic saline solutions or sterile and injectable solutions which contain dispersion agents and/or pharmacologically compatible solubilizing agents, for example propyleneglycol or butyleneglycol.

Thus, to prepare an aqueous solution injectable by the intravenous route a cosolvent may be used an alcohol such as ethanol, a glycol such as polyethyleneglycol or propyleneglycol and a hydrophilic surfactant such as polysorbate 80. In order to prepare an injectable oily solution injectable by the intramuscular route, the active ingredient may be solubilized by a triglyceride or a glycerol ester.

For transdermal administration, it is possible to use patches in multilaminated form or with a reservoir in which the active ingredient is in alcoholic solution.

The active ingredient may also be formulated in the form of microcapsules or microspheres, optionally with one or more vehicles or additives.

The active ingredient may also be presented in the form of a complex with cyclodextrin, for example a-, b- or g- cyclodextrin, 2-hydroxypropyl-b -cyclodextrin or methyl-b-cyclodextrin.

Among the prolonged release forms useful in the case of chronic treatments, it is possible to use implants. These latter may be prepared in the form of oily suspensions or in the form of suspensions of microspheres in an isotonic medium.

According to the present invention the oral forms of administration are preferred.

EXAMPLE 1: Capsule containing 0.1 mg of (1Z,2E)-1-(2-fluorophenyl)-3-(4-hydroxyphenyl)-prop-2-en-1-one-O-(2-dimethylaminoethyl)-oxime.

| | |
|---|---|
| Compound A | 0.118 mg |
| Crystallized, extra fine lactose monohydrate | 99.132 mg |
| Modified maize starch | 25 mg |
| Anhydrous colloidal silica | 0.11 mg |
| Magnesium stearate | 0.64 mg |
| For an opaque white capsule, size 0, finished at | 125 mg |

EXAMPLE 2: Capsule containing 1.0 mg of (1Z,2E)-1-(2-fluorophenyl)-3-(4-hydroxyphenyl)-prop-2-en-1-one-O-(2-dimethylaminoethyl)-oxime.

| | |
|---|---|
| Compound A | 1.18 mg |
| Crystallized, extra fine lactose monohydrate | 451.42 mg |
| Modified maize starch | 114 mg |
| Anhydrous colloidal silica | 0.5 mg |
| Magnesium stearate | 2.9 mg |
| For an opaque white capsule, size 0, finished at | 570 mg |

EXAMPLE 3: Capsule containing 5 mg of (1Z,2E)-1-(2-fluorophenyl)-3-(4-hydroxyphenyl)-prop-2-en-1-one-O-(2-dimethylaminoethyl)-oxime.

| | |
|---|---|
| Compound A | 5.9 mg |
| Crystallized, extra fine lactose monohydrate | 446.7 mg |
| Modified maize starch | 114 mg |
| Anhydrous colloidal silica | 0.5 mg |
| Magnesium stearate | 2.9 mg |
| For an opaque white capsule, size 0, finished at | 570 mg |

EXAMPLE 4: Capsule containing 10 mg of (1Z,2E)-1-(2-fluorophenyl)-3-(4-hydroxyphenyl)-prop-2-en-1-one-O-(2-dimethylaminoethyl)-oxime.

| | |
|---|---|
| Compound A | 11.8 mg |
| Crystallized, extra fine lactose monohydrate | 440.8 mg |
| Modified maize starch | 114 mg |
| Anhydrous colloidal silica | 0.5 mg |
| Magnesium stearate | 2.9 mg |
| For an opaque white capsule, size 0, finished at | 570 mg |

What is claimed is:

1. A method for the treatment of sleep apnea syndrome which comprises administering to a patient in need of such treatment an effective amount of 1-(2-fluorophenyl)-3-(4-hydroxyphenyl)-prop-2-en-1-one-O-(2-dimethylaminoethyl)-oxime or of one of its pharmaceutically acceptable salts.

2. A method according to claim 1 wherein the compound is the hemifumarate of (1Z, 2E)-1-(2-fluorophenyl)-3-(4-hydroxyphenyl)-prop-2-en-1-one-O-(2-dimethylaminoethyl)-oxime.

3. A method for the treatment of sleep obstructive apnea-hypoapnea syndrome which comprises administering to a patient in need of such treatment an effective amount of 1-(2-fluorophenyl)-3-(4-hydroxyphenyl)-prop-2-en-1-one-O-(2-dimethylaminoethyl)-oxime or of one of its pharmaceutically acceptable salts.

4. A method according to claim 3 wherein the compound is the hemifumarate of (1Z, 2E)-1-(2-fluorophenyl)-3-(4-hydroxyphenyl)-prop-2-en-1-one-O-(2-dimethylaminoethyl)-oxime.

* * * * *